United States Patent

Bäther et al.

Patent Number: 5,464,588
Date of Patent: * Nov. 7, 1995

[54] ARRANGEMENT FOR COLORIMETRICALLY DETECTING A GASEOUS AND/OR VAPOROUS COMPONENT IN A GAS MIXTURE

[75] Inventors: Wolfgang Bäther; Rainer Bommer, both of Lübeck, Germany

[73] Assignee: Drägerwerk Aktiengesellschaft, Lübeck, Germany

[ * ] Notice: The portion of the term of this patent subsequent to Mar. 14, 2012, has been disclaimed.

[21] Appl. No.: 194,274

[22] Filed: Feb. 10, 1994

[30] Foreign Application Priority Data

Feb. 10, 1993 [DE] Germany ............... 43 03 861.1

[51] Int. Cl.⁶ ................................ G01N 30/88
[52] U.S. Cl. ............. 422/88; 422/58; 422/61; 422/82.05; 436/44
[58] Field of Search ............. 422/54–58, 82.05, 422/81, 53, 88, 61; 436/43, 44, 46

[56] References Cited

U.S. PATENT DOCUMENTS

| | | | |
|---|---|---|---|
| 4,235,097 | 11/1980 | Kring et al. | 422/88 |
| 4,913,881 | 4/1990 | Evers | 427/88 |
| 4,933,144 | 6/1990 | Moy | 422/88 |

Primary Examiner—Lyle A. Alexander
Attorney, Agent, or Firm—Walter Ottesen

[57] ABSTRACT

One or more reaction zones, formed as channels into a carrier, are each lined with a color indicator. This carrier is improved so that the reaction zones can be coated with the required indicators with uniform coating thickness. The coating can be individually changed and can be easily provided. The above is achieved with a carrier which is subdivided into an upper part and a lower part and a sandwich-like composite foil is held between these parts. A reagent carrier foil of the composite foil is provided with the reaction zones and is covered with a channel foil which delimits the reaction zones to have a channel-like shape. An especially advantageous configuration for the reaction zones is provided by an aperture matrix in which carrier spherules are accommodated. The carrier spherules are impregnated with the indicator.

15 Claims, 5 Drawing Sheets

ARRANGEMENT FOR COLORIMETRICALLY DETECTING A GASEOUS AND/OR VAPOROUS COMPONENT IN A GAS MIXTURE

FIELD OF THE INVENTION

The invention relates to an arrangement for colorimetrically detecting gaseous and/or vaporous components in a gas mixture which penetrates into one or more channel-shaped reaction zones machined into a carrier. A color indicator is applied to the base surface of the reaction zones and this color indicator enters into a color reaction with the component to be detected.

BACKGROUND OF THE INVENTION

An arrangement of the above kind is disclosed in U.S. Pat. No. 5,089,232.

In the known arrangement, channel-shaped recesses are worked into a carrier. These recesses hold respective color indicators and additional reaction partners for the colorimetric detection reaction. The reaction partners can be identical in each of the channels or they can be different depending upon whether a multiple detection of the same gas component is to be carried out or if a detection of different gas components in air is to be carried out. Each of the channels has at least one inlet opening for the toxic substance to be detected which is either drawn by suction through the channel or diffuses into the channel. Each individual channel thereby operates as a conventional individual testing tube for the colorimetric detection of gaseous components in air. A multiple measuring device in miniaturized form for the colorimetric detection of gaseous toxic substances is obtained with the arrangement of several channels arranged one parallel to the other on the carrier. The chip-shaped carrier is evaluated by an optoelectronic scanning apparatus. For this purpose, a transmitting and detecting unit is guided at the same elevation and in identical length to each of the individual channels and the light reflected from the colored channel zone is evaluated. The length of the coloration zone provides information as to the concentration contained in the detection sample or the quantity of the gaseous component to be investigated in dependence upon whether the channels are configured as testing tubes for throughflow or as dosimeters for diffusion of tile toxic substance.

In the known arrangement, the reaction zones are produced as channels in the base structure of the carrier material and they are in the form of recesses having a shallow depth. The subsequent coating of the channel recesses is possible only under difficult manufacturing conditions and produces an unsatisfactory result with respect to a uniform distribution of the reaction partners, especially of the color indicator along the entire length of the channel recesses. This is especially caused by introducing the reaction partners from a liquid emulsion so that a distribution of the reaction partner in a nonuniform density occurs within the channel because of surface tensions of the liquid and because of nonuniform distribution of the solid constituents in the suspension.

This situation is made still more critical when different reagent carriers for detecting various gaseous components are utilized in the different channels so that also different suspensions are used having different surface tensions and different solid reaction carriers with the solid reaction carriers being distributed in the suspension. A nonuniform distribution of the reaction partners along the channels can result in a fluctuation of the color indication which is not caused by the toxic substance to be detected and leads to the falsification of the measuring result.

SUMMARY OF THE INVENTION

It is an object of the invention to improve a carrier of the above-mentioned kind so that an individually changeable application of the reaction zones can be realized which is simple to carry out with the reaction zones having the required indicators or adsorbent materials with uniform coating density and with the indicators being different as may be required. Of special importance is the possibility of a complete conversion of the toxic substance to be detected at the color indicators or a complete collection in the adsorbent materials.

The arrangement of the invention is for colorimetrically detecting a gaseous and/or vaporous component in a gas mixture and includes: a reagent carrier band having a surface; a color indicator containing reagents capable of entering into a color reaction with the component; the color indicator being in the form of a surface spread along a predetermined path on the surface to define a reaction zone; channel carrier means having mutually adjacent side walls formed therein and being disposed on the surface for causing the side walls and the path to conjointly define a channel; and, channel access means for facilitating the penetration of the gas mixture into the channel to permit the component to enter into a color reaction with the color indicator in the reaction zone.

A manufacturing technology can be utilized which is optimized for each individual work step because of the breakdown of the elements, which are required for forming the detection channels, in assembly groups suitable for the preparation of the lining of the channel-shaped reaction zones, that is, in an essentially flat reagent carrier band, on the one hand, and a channel carrier forming the side walls, on the other hand. In this way, the reaction zone on the reagent carrier band can be formed by means of known techniques for applying liquids to the surface. For this purpose, for example, a mask which predetermines the course of the reaction zone is placed over the reagent carrier band and the exposed cutouts of tile mask are filled with the liquid necessary for the corresponding detection. The liquid after vaporization or drying of the solvent leaves the reaction partner, especially the color indicator, in a solid form. The reaction zone remains as a track on the reagent carrier band after the mask is removed.

Problems of different surface tensions or inadequately uniform distribution of the reaction partners along the reaction zone are eliminated since no limitation with respect to a uniform application of the suspension solution because of the channel walls must be tolerated. After the reaction zone dries, the reagent carrier band is applied to the channel carrier, for example, to the lower side of the channel carrier, for example, by adhesive. The reaction carrier band and the reaction zones thereof conjointly form the particular base surface for a reaction channel having side walls which are formed by the channel carrier. If necessary, the channel carrier is provided with a thin cover plate by means of which the channels are covered with respect to each other and with respect to the ambient. The channel carrier can, however, be provided with a one-piece cover for the channel walls so that a separate cover plate is unnecessary.

The reagent carrier band can have a large area serving as a base surface for several channels at the same time, or the reagent carrier band can define the base surface strip shaped for each channel individually and must then be applied or placed with adhesive as individual strips individually on the channel carrier and follow the channel course.

The reagent carrier band and/or the channel carrier can be made of plastic in the form of thin platelets (material thickness approximately 2 mm) and of suitable material resistant to the reagents. However, it is especially advantageous to configure the reagent carrier band, the channel carrier and, if required, an additional cover plate covering the channels as thin foils which are assembled to a sandwich-like composite foil. The channel foil has breakthroughs which correspond in their form and in their dimensions to the reaction zones. Each of the foils is approximately 75 to 100 micrometers thick. Preferably, glass, ceramic, metal or transparent perfluorinated hydrocarbons such as perfluoropropylene ethylene (FEP) can be used as foil materials.

It is advantageous to assemble the carrier from a stable carrier upper part and a carrier lower part between which the reagent carrier band is accommodated in position with or without cover plate, that is, the entire composite foil. This assembly increases the stability of the reagent carrier band and of the composite foil.

In all cases, that region of the reagent carrier band and/or the cover plate as well as the carrier upper part must be transparent for the radiation required for the evaluation in order that a colorimetric evaluation can be made. The radiation is the visible light if an evaluation by the user is adequate, that is, an evaluation which the user can carry out simply by viewing with the eye. Otherwise, the transparency has to be provided for the corresponding radiation when an electrical evaluation device is provided which uses special detectors utilizing special infrared light or light of a particular wavelength.

An embodiment in the form of a composite foil configuration can be more advantageously assembled into a device because, in this case, and after drying of the reaction zone (applied from the liquid phase), the channel foil can be applied to the reaction carrier foil coincident to the course of the reaction zones. The channel foil has breakthroughs which define channel walls next to each individual reaction zone. Here too it is advantageous that the channel structure is worked into a foil since the channel structure can be configured in a simple form as a foil cutout which, in turn, must not be lined with the indicator. The legs or struts which remain between each two adjacent cutouts or breakthroughs can be easily welded to the reagent carrier foil disposed therebelow to form a unit so that adjacent channels are closed off sealtight with respect to each other and with respect to the ambient. The cover foil is placed over the channel cutouts and closes off the channel walls. The start and/or end of the closed channels formed in this manner are provided with a channel opening through which the component to be detected has access to the reaction zones. The component to be detected can, for example, be a toxic substance. The channel openings can, in turn, be sealed by foil membranes which are, at the same time, components of the additional cover foil applied over the channel foil. This seal is punctured when the carrier is used as a testing tube. This puncturing can be mechanical or by connecting a suction pump for establishing a throughflow of the channel as disclosed in U.S. Pat. No. 5,089,232 which is incorporated herein by reference.

Further possibilities of applying the reaction emulsion to the reagent carrier foil comprise that preprepared strips define the reaction zone as channel surfaces. For this purpose, for example, large-area carrier materials, such as paper (cellulose) or plastic foil, are impregnated with the indicator and thereafter cut into strips which are then applied to the reagent carrier band with adhesive or themselves define the reagent carrier band. The impregnation is either direct (for example, on paper) or impregnated silica gel or aluminum oxide is applied to the reagent carrier band made of glass or ceramic.

Furthermore, for a generic carrier, this task can be solved in that, in lieu of a surface reaction zone, the carrier has one or more capillary tubes lined with reagents with the capillary tubes being applied to the reagent carrier band. The tubes are then covered with a channel foil and, at their ends, the channel foil has at least one sealed channel connection through which the toxic substance to be detected is given access to the capillary tube. The capillary tubes can also be applied with adhesive to the reagent carrier band so that the channel foil serves more as a protective covering and provides only an insignificant contribution to the attachment of the tubes. The capillary tubes are to be seen as reaction channels having linings of reagents which define the reaction zones. The finished capillary tubes (lined in a separate coating work step) can be applied to the reagent carrier band in a simple manner.

It is advantageous to provide the reaction zones on the reagent carrier foil as an aperture matrix in order to increase the uniformity of the distribution of the reaction partners for the colorimetric reaction along the reaction zone and thereby generate a spatially defined expansion of the indicator. Especially the indicator itself should be so distributed. In this way, a quantitative chemical conversion which is as reproducible as possible is obtained when a carrier gas is passed by, which is enriched with the gas component to be detected. Carrier spherules are placed in the aperture matrix which, in turn, are impregnated with the color indicator. In this way, predefined receiving locations are assigned to the indicator so that the uniformity of the indicator distribution along the reaction zone is still further increased. Here too, the preparation of the reaction zone itself is still further subdivided into additional manufacturing steps which can each be controlled separately, on the one hand, for the introduction or production of an aperture matrix and, on the other hand, for the distribution of the impregnated carrier spherules in the holes provided. The impregnation of these carrier spherules is itself a reproducible manufacturing operation which can be controlled in an excellent manner.

This configuration of the reagent carrier foil is of very great significance because uniformity and reproducibility of distribution of the reaction partners along the course of the channel are very important in the miniaturization of the carrier and the miniaturization of the testing tubes or dosimeter tubes. This is especially so for the case where several reaction zones are assembled into an array on a chip-shaped carrier.

The size of approximately 100 micrometers for the aperture diameter and approximately 125 micrometers for the spherule diameter has proven to be advantageous. When an aperture matrix of this kind is charged, a vacuum is generated on one side of this foil whereby the spherically-shaped carriers are drawn by suction into the apertures. The underpressure increases on the vacuum end surface of the foil because of this self sealing. This underpressure continues until the surface of the foil is completely charged when all pregiven apertures are occupied. Excess spherules can be removed with pressurized air. A further advantage of the aperture matrix is that defined intermediate spaces are formed between the carrier spherules which generate a reproducible flow resistance for the gas sample, which is to detected, through the flow channel and makes possible an intensive contact between the toxic substance gas and the reagent material.

The carrier spherules are made of silica gel which is produced in an advantageous manner according to the so-called sol-gel process which is described in U.S. Pat. No. 4,505,985 incorporated herein by reference. When the sol-gel process is used to produce the spherules from silica gel, the advantage is afforded that the spherules can be more easily modified in accordance with requirements. Thus, necessary indicators can be introduced directly into the spherule volume whereby a more homogeneous distribution, especially on the sphere surface, is obtained. Other chemicals can be built into the spherule structure such as functional groups which immobilize indicator substances, have desired hydrophobic characteristics and also realize the porosity which is desired.

The reagent carrier foil with the channel foil is protected against external damage by means of a base foil and a protective foil. In this way, manipulation during the production of the complete carrier is more reliable.

Advantageous materials for the carrier foil comprise either ceramic, glass or metal. PTFE has been proven advantageous as a plastic material for the foils. If all foils are made of the same plastic material, then a reliable thermal welding is possible, for example, by means of a laser beam.

The material perfluoropropylene ethylene (FEP) provides a significant characteristic with respect to the adherence for the substances to be applied and the indicators. This is that much more surprising because it is a type of PTFE but nonetheless has better wetting characteristics for the polar reagents and indicator substances. These reagents are mostly applied in the liquid phase. Also, the manipulation of thinnest foils of FEP does not lead to an exfoliation of the layer for the reaction zones.

Several component regions disposed one behind the other in the reaction zone are advantageously provided when no directly indicating color reagent is available for the toxic substance to be detected or when the color reagents cannot be produced in a simple manner and yet still have long-term stability. For such cases, a conversion layer is placed forward of the indicator layer which contains such reagents which chemically decompose the component to be detected into reaction products from which at least one reaction product enters into a color reaction with the next-following indicator layer. The reagents known from conventional testing tube technology can be selected as suitable conversion regions (forward or upstream layers) and indicator regions.

The composite foil configuration or the application of reaction zones of different detection sensitivity onto the reaction carrier band can also be advantageously utilized in that a plurality of area reaction zones are applied to the reagent carrier band so as to define several component regions. The area reaction zones can be configured to be circular in shape or to be strip shaped. The component regions are provided with different indicators which react to different components to be detected by correspondingly different colorations. The reaction zones are either separated from each other by the channel carrier or are all simply enclosed by the channel carrier. In all cases, a cover foil is placed over the channel carrier and partitions the reaction zones from the ambient. The cover foil can be simply pulled off the channel carrier for detecting toxic gas components in the ambient which may be present. In this way, all reaction zones or their component regions are simultaneously exposed to the ambient atmosphere. A conclusion as to the presence of a corresponding toxic substance to be detected can be drawn from a corresponding coloration of the exposed reaction zones. The depth of coloration is a semi-quantitative indication for the quantity of toxic substance.

Devices of this kind are utilized under the designation "test badges" in order to screen in a toxic substance atmosphere, which is initially unknown, which toxic substances are present and, if present, in what suspected concentration. Subsequently, the presence and quantity of the toxic material can be ascertained with the use of more precise quantitative indicating measuring systems.

A further possibility to detect gaseous or vaporous toxic substances comprises that these substances are retained and collected in an adsorbent material in order to be chemically or physically removed from the adsorbent material after the test sample is taken and to be quantitatively determined. Devices configured in this manner serve for long-term measurements and are characterized as collecting test devices or long-term dosimeters.

The known devices can be improved in this manner by making it possible to provide a simple charge of the channels with the adsorbent material. For this purpose, open reaction channels in the carrier are filled with the adsorbent material and the carrier is configured as a reaction carrier band. The reaction channels are covered with a channel carrier covering the channels so that the channels are sealed with respect to each other and with respect to the ambient. The respective channel connections are left accessible.

Active carbon is appropriate as a charge because of its large-area adsorption capacity. The active carbon charged with the component to be detected is removed from the channels for evaluation and analyzed pursuant to a wet-chemical process and the adsorbed quantity is determined. The reagent carrier band is releasably joined to the channel carrier in order to be able to easily remove the adsorbent material from the channels so that both are separated from each other for removing the charged adsorbent material whereupon the filled channels are accessible.

Other suitable adsorbent materials are organic polymers such as polyphenylene oxide obtainable under the trade name TENAX or molecular sieves (zeolite). These afford the advantage that the adsorption of the component to be detected takes place exclusively on their surfaces so that they can be easily desorbed with the application of heat and be subjected to a gas analysis. A suitable zeolite (molecular sieve) can be selected in dependence upon the type and adsorption capacity of the component to be detected. Alternating layer sequences of the components active carbon, TENAX, zeolite can be filled into the channels.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
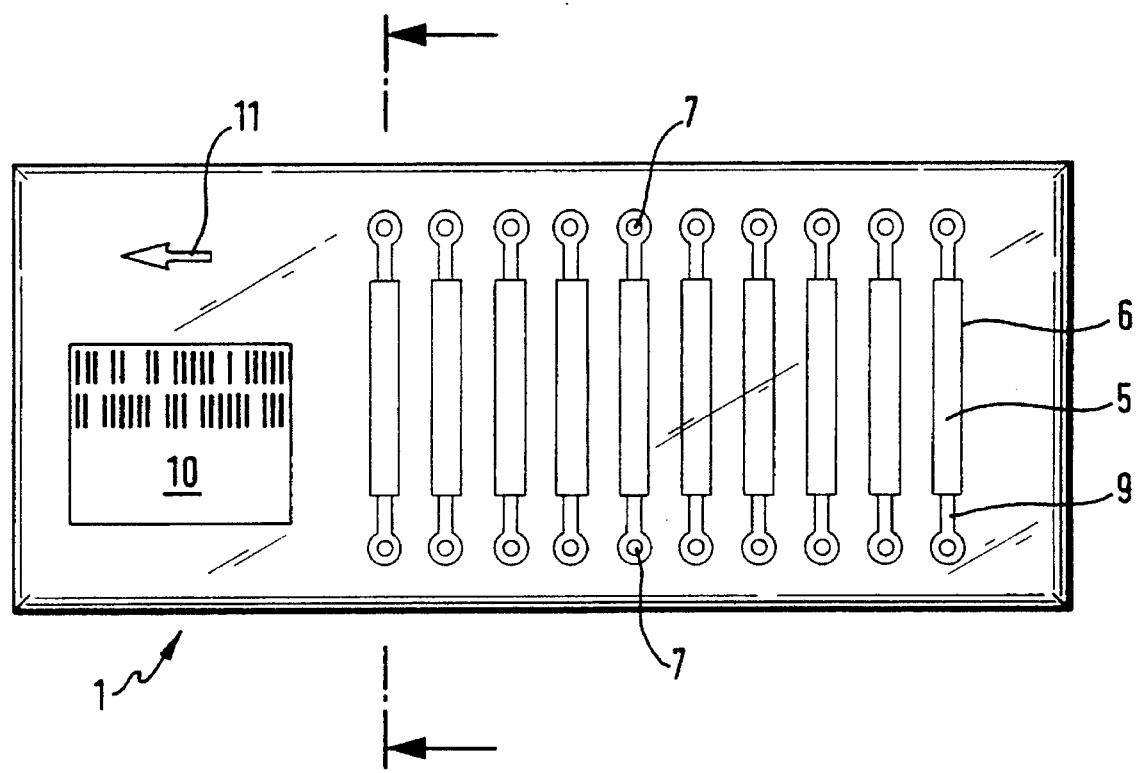
FIG. 1 is a plan view of a chip-shaped carrier having several reaction zones.
Figure 2:
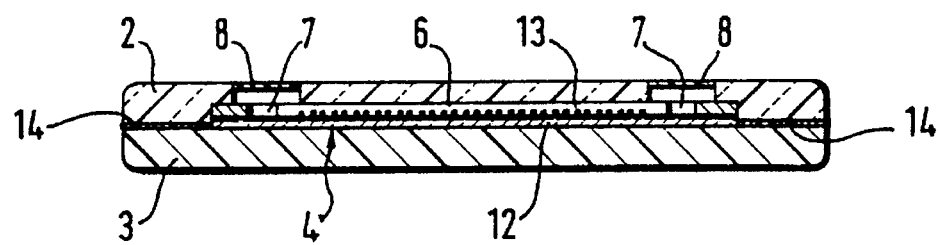
FIG. 2 is a section view taken through the carrier of FIG. 1 along a channel-shaped reaction zone.

A chip-shaped carrier 1 is shown in FIG. 1 and comprises a carrier upper part 2 and a carrier lower part 3 as shown in FIG. 2. A composite foil 4 is held between the parts (2, 3). The upper part 2 comprises a transparent plastic material and permits ten parallelly running reaction zones 5 to be freely viewed. Each reaction zone is configured as a base surface for a reaction channel 6. Access openings 7 are provided at the ends of the channel 6 through which the gas mixture to be detected can be drawn through by suction with a pump (not shown) or, in the case of an opening only at one end, so that the gas mixture can migrate to the reaction zone 5 along the channel 6. The access openings 7 are closed with a seal 8 as shown in FIG. 2 which is punctured for carrying out a measurement. The access openings 7 are connected to the channels 6 via a channel connection 9.

A data field 10 is printed on tile surface of the carrier upper part 2 and provides technical information and instructions for the use of the colorimetric detection device. This information can be read either by the user or can be detected by an evaluation unit (not shown) with the aid of a bar code. An evaluation device of this kind is described in U.S. Pat. No. 5,089,232 incorporated herein by reference. A direction arrow 11 indicates which end of the carrier 1 is to be inserted first into the evaluation unit. The data field 10 is read out during the insertion and the information contained therein is transmitted to the evaluation unit.

The carrier 1 is inserted so far into the evaluation unit until the first non-used reaction channel 6 reaches the optical evaluation unit.

The evaluation unit includes an arrangement of light sources and receivers which, at a specific wavelength, scan the coloration along the course of the reaction zone 5. At the same time, and after puncturing the seal 8, a pump is connected which draws the gas to be investigated through the channel 6 by suction. The reaction zone 5 colors more or less in dependence upon the content of the gas component in the gas. This coloration is detected by the evaluation unit and is processed to a measurement value. An automatic transport to the next-adjacent second channel 6 takes place after evaluation of the first channel 6 is completed. Evaluation of the second channel takes place in the same manner as described. Up to ten different gases, as required, can be investigated and measured in this way.

FIG. 2 is a section view along the length of a channel 6 of the carrier 1 of FIG. 1 with the composite foil 4 containing a reagent carrier foil 12 in the form of an aperture matrix. The aperture matrix 12 has accommodated a defined number of carrier spherules which are exposed in the channel 6 to the gas to be investigated. The carrier upper part 2 has the seal 8 located over the access openings 7. The seal 8 is punctured in order to, for example, connect to a pump (not shown) for pumping the gas. The gas to be detected passes via the access opening 7 to the channel 6 and therewith to the indicator applied to the carrier spherules 13. The carrier upper part 2 is joined about the periphery to the carrier lower part 3 via an adhesive seam 14 whereby the composite foil 4 is held between the two parts (2, 3).

Figure 3:
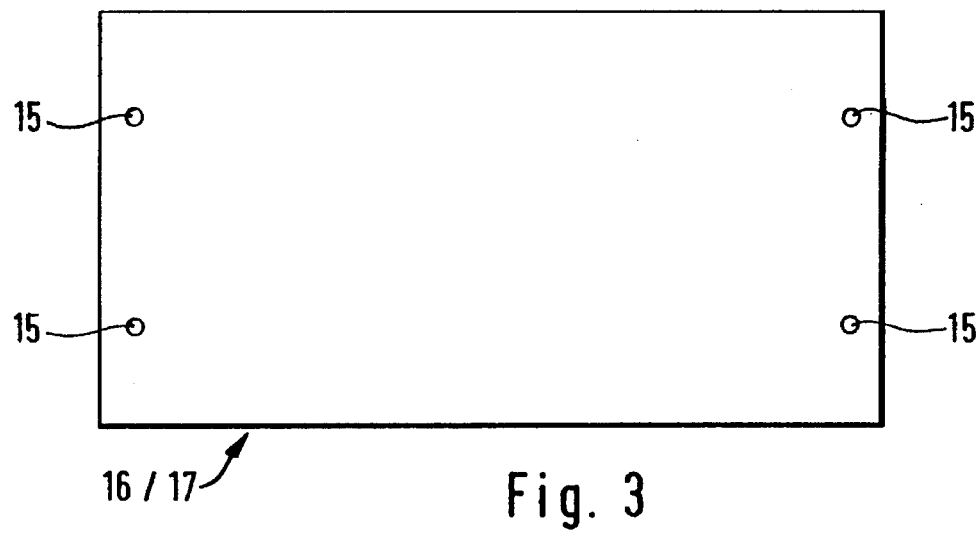
FIG. 3 is a plan view of the base foil or the cover foil.

The base foil shown in FIG. 3 comprises only a rectangular foil of plastic having four centering or attachment holes 15 in its respective corner regions. This same base foil 16 can also be utilized as a cover foil 17.

Figure 4:
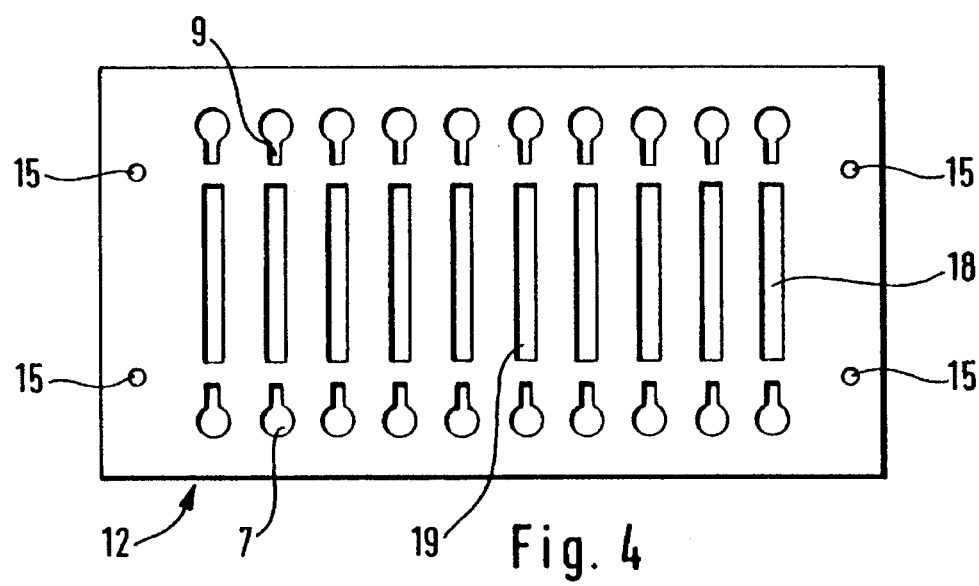
FIG. 4 is a plan view of the reagent carrier foil.

The reagent carrier foil 12 of FEP is shown in FIG. 4 and has individual tracks as reaction zones 18 with the tracks being mutually parallel. The tracks are coated with the reagents required for the colorimetric detection. The reaction zones can either comprise a coating 19 of indicator solution applied from a suspension but can also be configured as an aperture matrix filled with the carrier spherules 13 (see FIG. 6). The reagent carrier foil 12 likewise has through-punched access openings 7 with corresponding channel connections 9. Centering holes 15 are likewise provided on the reagent carrier foil 12 as a positioning aid and are coincident with the centering holes provided on the base foil 16.

Figure 5:
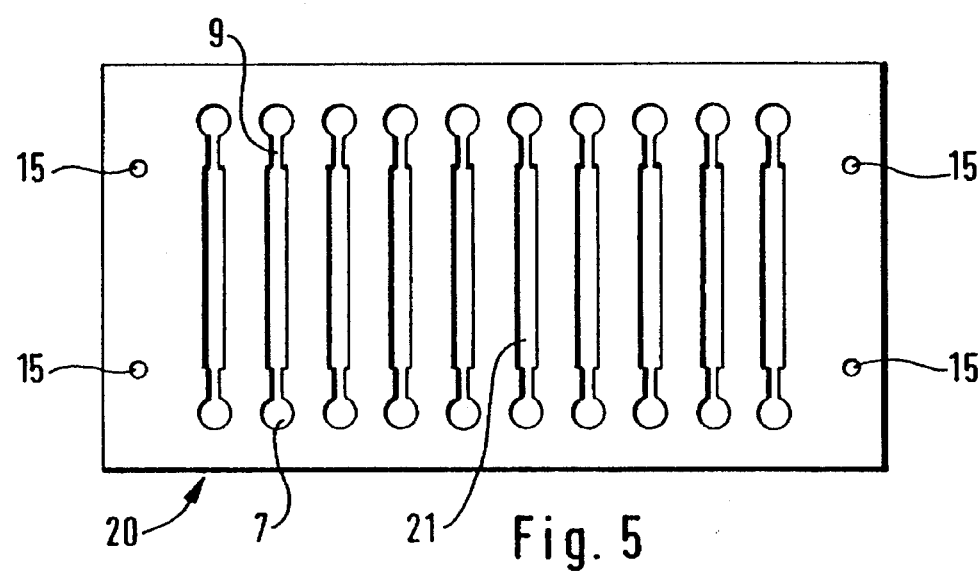
FIG. 5 is a plan view of the channel foil.

The channel foil 20 of FIG. 5 includes breakthroughs 21 which coincide with the course of the reaction zones 18. The breakthroughs serve as channels for the gas components to be investigated. A connection to the access opening 7 is provided to each of the breakthroughs 21 via the channel connection 9. The breakthroughs 21 of the channel later define the channel walls when the channel foil 20 is applied to the reagent carrier foil 12. The cover foil 17 is applied to the channel walls which then partitions the channels 21 from each other as well as from the ambient.

Figure 6:
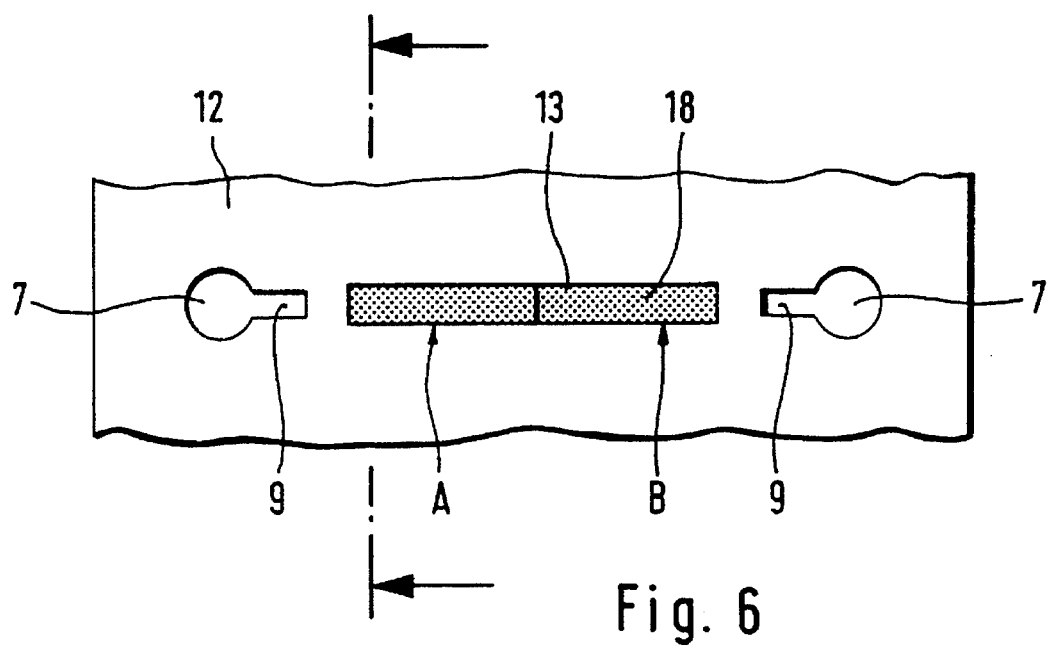
FIG. 6 is a detail view of a reaction zone in the form of an aperture matrix.
Figure 7:
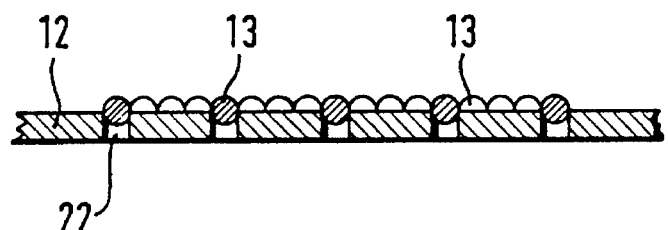
FIG. 7 is a detail section view taken through the aperture matrix of FIG. 6.

An example of an aperture matrix 18 as a reaction zone is shown in FIG. 6. FIG. 6 is a cutaway portion and shows only a single reaction zone 18. The aperture matrix 18 is filled with carrier spherules 13 and is shown in section in FIG. 7 which shows the carrier spherules 13 in the apertures 22 of the reagent carrier foil 12. Each individual reaction zone 18 defines an individual aperture matrix but also the entire reagent carrier foil 12 can be seen as a complete aperture matrix. The reaction zone 18 is subdivided into component regions A and B with the component region A carrying a coating which chemically converts the component to be detected into such a product that enters into a color reaction with the color indicator provided in region B when the component flows from region A to region B. Component region A is a conversion layer and component region B is an indicator layer.

Figure 8:
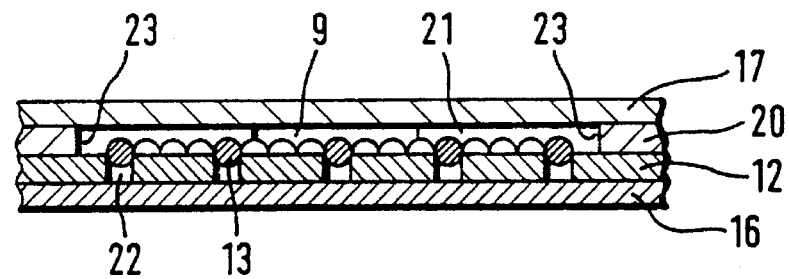
FIG. 8 is a detail side elevation view, in section, showing a composite foil comprising cover foil, channel foil, reagent carrier foil and base foil.

The packet comprising the base foil 16, reagent carrier foil 12 in the form of an aperture matrix, channel foil 20 and cover foil 17 is shown in FIG. 8 as a packet joined to form a composite foil 4. The section shows the view along a channel 21 looking toward the opening of the channel connection 9. The channel 21 is formed laterally by the walls 23 of the breakthrough provided in the channel foil 20 and the upper end of the channel is closed by the cover foil 17. The reaction zone 18 is the sum of the surface of each carrier spherule 13 which projects into the channel 21.

Figure 9:
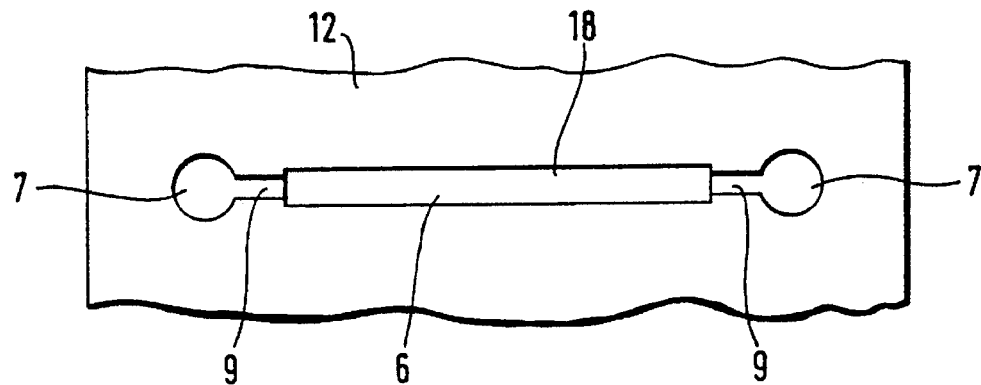
FIG. 9 is a detail view of a reaction zone in the form of a capillary tube which is coated on the inside thereof.

FIG. 9 shows a further example for a reagent carrier foil 12 on which a plurality of capillary tubes is applied as channels 6 having a lining 18 as a reaction zone of which only one is shown. The capillary tube 6 has channel connections 9 at respective ends thereof which open into tile access opening 7.

Figure 10:
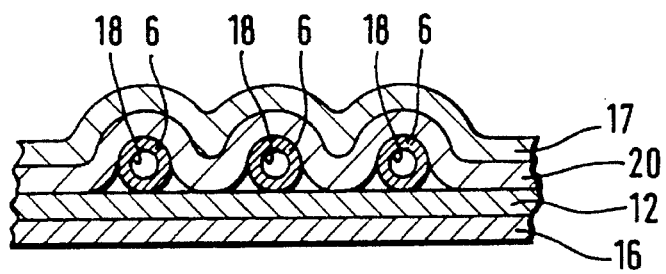
FIG. 10 is a section view taken through a composite foil having several capillary tubes.

A partial section view is shown in FIG. 10 which is taken through the composite foil 4. Three capillary tubes are placed as channels 6 on the carrier foil 12 of-the composite foil 4. The channels are coated with an inner lining 18 of reagents which cannot be shown separately because of the small scale of the drawing. The channel foil 20 is placed over the tubes 6 and the foil 20 covers the tube 6 as well as the carrier foil 12 except for those surface parts which are left open for the access openings 7 (see FIG. 9). These surface parts are then subsequently provided with a seal 8 (see FIG. 2) which is punctured when used.

Figure 11:
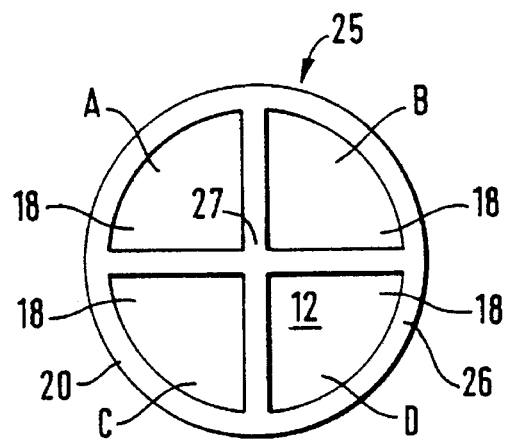
FIG. 11 is a view of a testing badge.

FIG. 11 is a view of a testing badge 25 having a reagent carrier band 12 on which the reaction zone 18 is subdivided by the channel carrier 20 into four component regions (A, B, C, D) . The channel carrier 20 is in the form of a strut structure encompassing the regions (A, B, C, D) and has an inside cross 27 for partitioning the regions (A, B, C, D) and is cemented to the reagent carrier band 12 lying below the plane of the drawing. A cover foil (not shown) is placed over the channel carrier 20 above the plane of the drawing. For detecting toxic substances, the cover foil is either punctured so that individual component regions (A, B, C, D) are exposed to the ambient atmosphere or the cover foil is simply completely pulled off so that all component regions (A, B, C, D) are exposed at the same time.

Figure 12:
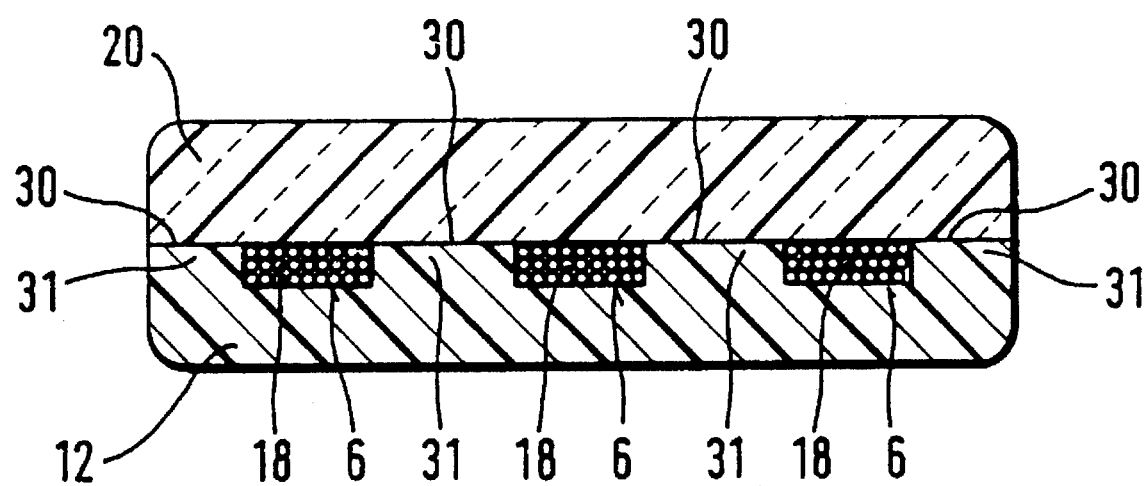
FIG. 12 is a section view taken through a carrier filled with an adsorbent material.

A carrier is shown in FIG. 12 which is suitable for such cases wherein no colorimetric detection is required or wanted; instead, it is only desired to collect the component to be detected over a specific time span and to make the determination by means of separate analysis methods. The carrier shown in FIG. 12 includes a reagent carrier band 12 in the form of a plastic plate into which channels 6 are formed. The channels are shown here in cross section perpendicular to their flow direction or diffusion direction. The channels 6 are filled with an adsorbing material 18 which can comprise small grains of active carbon. The channels 6 filled in this manner are sealed with respect to each other and with respect to the ambient by a channel carrier 20. The contact surfaces 30 on the struts 31 between the reagent carrier band 12 and the channel carrier 20 are made gas-tight by cementing. In FIG. 12, the channels 6 are formed into the reagent carrier band 12 and are covered with the smooth surface channel carrier 20. Likewise, the channels 6 can be formed in the channel carrier 20 and the reagent carrier band 12 closes the channels 6 with a smooth continuous surface.

It is understood that the foregoing description is that of the preferred embodiments of the invention and that various changes and modifications may be made thereto without departing from the spirit and scope of the invention as defined in the appended claims.

What is claimed is:

1. An arrangement for colorimetrically detecting a gaseous and/or vaporous component in a gas mixture, the arrangement comprising:

a reagent carrier band having a surface;

a color indicator containing reagents for entering into a color reaction with said component;

said color indicator being in the form of a plurality of surface spreads along respective predetermined paths on said surface of said reagent carrier band to define a plurality of respective reaction zones;

channel carrier means for defining a plurality of pairs of mutually adjacent side walls formed therein and being disposed on said surface for causing each pair of said side walls and the path corresponding thereto to conjointly define a channel;

separate channel access means for each one of the channels to facilitate the penetration of said gas mixture into said one channel to permit said component to enter into a color reaction with the color indicator in the reaction zone of said channel to provide a colorimetric indication of the component;

said reagent carrier band and said channel carrier means being first and second foils;

each pair of said side walls being defined by a cutout in said second foil and said second foil having a plurality of said cutouts defining corresponding pairs of said side walls;

a third foil covering said second foil and said channels to define a cover foil;

said cover foil being penetrable by radiation necessary for evaluating the coloration occurring in said reaction zone;

said first, second and third foils being sandwiched together to define a composite foil;

each one of said channels having a longitudinal end at or near the beginning of the path of the reaction zone of said one channel; and, each one of said separate channel access means being formed in said arrangement at or near said beginning of the reaction zone thereby permitting the coloration of the colorimetric detection to advance linearly along said path.

2. The arrangement of claim 1 further comprising a carrier upper part and a carrier lower part; said reagent carrier band being mounted fixed in position between said upper and lower parts; and, said upper part being transparent for the radiation required for the optical evaluation of said reaction zones.

3. The arrangement of claim 1, said first foil being made of a material selected from the group consisting of ceramic, glass and metal.

4. The arrangement of claim 1, said first foil being made of perfluoropropylene ethylene (FEP).

5. The arrangement of claim 1 said longitudinal end of each one of said channels being a first longitudinal end; each one of said channels having second longitudinal end at or near the end of the reaction zone; and, each one of said channels having channel exit means at or near the end of the reaction zone for permitting said gas mixture to exit from said one channel.

6. The arrangement of claim 1, each of said reaction zones being subdivided into a plurality of component regions arranged one behind the other in flow direction; and, said component regions having respective reaction partners different from each other.

7. The arrangement of claim 6, each of said reaction zones being subdivided into first and second component regions and said first component region being disposed upstream of said second component region; said second component region including said color indicator as a reaction partner and said first component region including a reagent for entering into a reaction with said component to produce a reaction product which can enter into a color reaction with said color indicator.

8. The arrangement of claim 1, said first foil defining a hole matrix and said arrangement further comprising a plurality of carrier spherules adheringly accommodated in corresponding ones of the holes of said hole matrix; and, said color indicator being impregnated on said carrier spherules.

9. The arrangement of claim 8, said carrier spherules being made of a material selected from the group consisting of silica gel, aluminum oxide and glass.

10. The arrangement of claim 8, said holes each having a diameter of approximately 100 micrometer and said spherule diameter being approximately 125 micrometer.

11. The arrangement of claim 10, said color indicator being a coating obtained from a suspension and applied to said first foil; and, said suspension comprising a color indicator dissolved in a solvent.

12. An arrangement for colorimetrically detecting a gaseous and/or vaporous component in a gas mixture, the arrangement comprising:

a carrier foil having a surface;

a plurality of capillary tubes;

a color indicator containing reagents for entering into a color reaction with said component;

said color indicator being in the form of a plurality of surface linings in corresponding ones of said capillary tubes to define respective reaction zones;

said capillary tubes being mounted on said surface to define respective paths thereon for said reaction zones;

said capillary tubes having respective open ends;

a cover foil covering said carrier foil and said capillary tubes to the extent that the open end of each capillary tube is partitioned spatially and with respect to flow from the open ends of the other capillary tubes and from the ambient;

access means for facilitating penetration of said gas mixture into said tubes to permit said component to enter into a color reaction with said color indicator in said reaction zone to provide a colorimetric indication of the component;

each one of said capillary tubes having a longitudinal end at or near the beginning of the path of the reaction zone of said one capillary tube; and, said access means being formed in said arrangement at or near said beginning of the reaction zone thereby permitting the coloration of the colorimetric detection to advance linearly along said path.

13. The arrangement of claim 12, said carrier foil being made of perfluoropropylene ethylene (FEP).

14. The arrangement of claim 12, said reaction zone being subdivided into a plurality of component regions arranged one behind the other in flow direction; and, said component regions having respective reaction partners different from each other.

15. The arrangement of claim 14, said reaction zone being subdivided into first and second component regions and said first component region being disposed upstream of said second component region; said second component region including said color indicator as a reaction partner and said first component region including a reagent for entering into a reaction with said component to produce a reaction product which can enter into a color reaction with said color indicator.

\* \* \* \* \*